(12) United States Patent
Weinberg

(10) Patent No.: US 7,594,916 B2
(45) Date of Patent: Sep. 29, 2009

(54) ELECTROSURGICAL FORCEPS WITH ENERGY BASED TISSUE DIVISION

(75) Inventor: Craig Weinberg, Denver, CO (US)

(73) Assignee: Covidien AG, Neuhausen Am Rheinfall (CH)

( * ) Notice: Subject to any disclaimer, the term of this patent is extended or adjusted under 35 U.S.C. 154(b) by 532 days.

(21) Appl. No.: 11/285,432

(22) Filed: Nov. 22, 2005

(65) Prior Publication Data

US 2007/0118111 A1 May 24, 2007

(51) Int. Cl.
*A61B 18/18* (2006.01)

(52) U.S. Cl. .............................. 606/51; 606/45; 606/50; 606/52

(58) Field of Classification Search .................... 606/45, 606/46, 48–51, 205–208
See application file for complete search history.

(56) References Cited

U.S. PATENT DOCUMENTS

| | | | |
|---|---|---|---|
| 371,654 A | 10/1887 | Brannan et al. | |
| 702,472 A | 6/1902 | Pignolet | |
| 728,883 A | 5/1903 | Downes | |
| 1,586,645 A | 6/1926 | Bierman | |
| 1,813,902 A | 7/1931 | Bovie | |
| 2,002,594 A | 5/1935 | Wappler et al. | |
| 2,011,169 A | 8/1935 | Wappler | |
| 2,031,682 A * | 2/1936 | Wappler et al. | 606/46 |
| 2,176,479 A | 10/1939 | Willis | |
| 2,279,753 A | 4/1942 | Knopp | |
| 2,305,156 A | 12/1942 | Grubel | |
| 2,632,661 A | 3/1953 | Cristofv | |
| 2,668,538 A | 3/1954 | Baker | |
| 2,796,065 A | 6/1957 | Kapp | |
| 3,459,187 A | 8/1969 | Pallota | |
| 3,643,663 A | 2/1972 | Sutter | |
| 3,651,811 A | 3/1972 | Hildebrandt et al. | |
| 3,720,896 A | 3/1973 | Beirlein | |
| 3,862,630 A | 1/1975 | Balamuth | |
| 3,863,339 A | 2/1975 | Reaney et al. | |

(Continued)

FOREIGN PATENT DOCUMENTS

CA 2104423 2/1994

(Continued)

OTHER PUBLICATIONS

Int'l Search Report EP 06 020574.7 dated Sep. 21, 2007.

(Continued)

*Primary Examiner*—Michael Peffley
*Assistant Examiner*—Vincent Sica

(57) ABSTRACT

An electrosurgical bipolar forceps for sealing and dividing tissue is disclosed. The forceps includes one or more shaft members having an end effector assembly disposed at a distal end thereof. The end effector assembly includes two jaw members movable from a first position to a second position wherein the jaw members cooperate to grasp tissue therebetween. Each of the jaw members includes an electrically conductive surface adapted to connect to a first energy source which communicates electrosurgical energy through tissue held therebetween. The forceps also include an energy-based cutting element adapted to connect to a second energy source and disposed between the jaw members. The energy-based cutting element is moveable from a first configuration when said jaw members are in the first position to a second configuration wherein the energy-based cutting element is disposed at an angle between the jaw members.

15 Claims, 5 Drawing Sheets

U.S. PATENT DOCUMENTS

| | | |
|---|---|---|
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,699 A | 10/1996 | Heimberger et al. |

| Patent No. | Date | Inventor(s) |
|---|---|---|
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,805 A | 11/1996 | Li |
| 5,578,052 A | 11/1996 | Koros et al. |
| 5,582,611 A | 12/1996 | Tsukagoshi et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,611,798 A | 3/1997 | Eggers |
| 5,620,453 A | 4/1997 | Nallakrishnan |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,688,270 A | 11/1997 | Yates et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,701 A | 7/1998 | McBrayer et al. |
| H1745 H | 8/1998 | Paraschac |
| 5,792,137 A | 8/1998 | Carr et al. |
| 5,792,177 A | 8/1998 | Kaseda |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,817,093 A | 10/1998 | Williamson, IV et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,860,976 A | 1/1999 | Billings et al. |
| 5,876,401 A | 3/1999 | Schulze et al. |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,984 A | 7/1999 | Sutcu et al. |
| 5,925,043 A | 7/1999 | Kumar et al. |
| 5,935,126 A | 8/1999 | Riza |
| 5,941,869 A * | 8/1999 | Patterson et al. ............ 604/508 |
| 5,944,718 A | 8/1999 | Dafforn et al. |
| 5,951,549 A | 9/1999 | Richardson et al. |
| 5,954,720 A | 9/1999 | Wilson et al. |
| 5,957,923 A | 9/1999 | Hahnen et al. |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,939 A | 11/1999 | Yoon |
| 5,989,277 A | 11/1999 | LeMaire, III et al. |
| 5,997,565 A | 12/1999 | Inoue |
| 6,004,335 A | 12/1999 | Vaitekunas et al. |
| 6,010,516 A | 1/2000 | Hulka et al. |
| 6,024,741 A | 2/2000 | Williamson et al. |
| 6,024,744 A | 2/2000 | Kese et al. |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,074,386 A | 6/2000 | Goble et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,123,701 A | 9/2000 | Nezhat |
| H1904 H | 10/2000 | Yates et al. |
| 6,126,658 A | 10/2000 | Baker |
| 6,152,923 A | 11/2000 | Ryan |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |

| Patent No. | Date | Inventor |
|---|---|---|
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |

| | | | | | |
|---|---|---|---|---|---|
| 7,169,146 B2 | 1/2007 | Truckai et al. | 2004/0254573 A1 | 12/2004 | Dycus et al. |
| 7,179,258 B2 | 2/2007 | Buysse et al. | 2004/0260281 A1 | 12/2004 | Baxter, III et al. |
| 7,195,631 B2 | 3/2007 | Dumbauld | 2005/0004564 A1 | 1/2005 | Wham et al. |
| D541,418 S | 4/2007 | Schechter et al. | 2005/0004568 A1 | 1/2005 | Lawes et al. |
| 7,207,990 B2 | 4/2007 | Lands et al. | 2005/0004570 A1 | 1/2005 | Chapman et al. |
| D541,938 S | 5/2007 | Kerr et al. | 2005/0021025 A1 | 1/2005 | Buysse et al. |
| 7,223,265 B2 | 5/2007 | Keppel | 2005/0021026 A1 | 1/2005 | Baily |
| 7,232,440 B2 | 6/2007 | Dumbauld et al. | 2005/0021027 A1 | 1/2005 | Shields et al. |
| 7,241,288 B2 | 7/2007 | Braun | 2005/0033278 A1 | 2/2005 | McClurken et al. |
| 7,241,296 B2 | 7/2007 | Buysse et al. | 2005/0096645 A1 | 5/2005 | Wellman et al. |
| 7,252,667 B2 | 8/2007 | Moses et al. | 2005/0101951 A1 | 5/2005 | Wham et al. |
| 7,255,697 B2 | 8/2007 | Dycus et al. | 2005/0101952 A1 | 5/2005 | Lands et al. |
| 7,267,677 B2 | 9/2007 | Johnson et al. | 2005/0107784 A1 | 5/2005 | Moses et al. |
| 7,270,660 B2 | 9/2007 | Ryan | 2005/0107785 A1 | 5/2005 | Dycus et al. |
| 7,270,664 B2 | 9/2007 | Johnson et al. | 2005/0113818 A1 | 5/2005 | Sartor et al. |
| 7,276,068 B2 | 10/2007 | Johnson et al. | 2005/0113819 A1 | 5/2005 | Wham et al. |
| 7,300,435 B2 | 11/2007 | Wham et al. | 2005/0113826 A1 | 5/2005 | Johnson et al. |
| 7,303,557 B2 | 12/2007 | Wham et al. | 2005/0113827 A1 | 5/2005 | Dumbauld et al. |
| 7,314,471 B2 | 1/2008 | Holman | 2005/0113828 A1 | 5/2005 | Shields et al. |
| 7,329,256 B2 | 2/2008 | Johnson et al. | 2005/0119655 A1 | 6/2005 | Moses et al. |
| 7,329,257 B2 | 2/2008 | Kanehira et al. | 2005/0149017 A1 | 7/2005 | Dycus |
| D564,662 S | 3/2008 | Moses et al. | 2005/0149151 A1 | 7/2005 | Orszulak et al. |
| 7,342,754 B2 | 3/2008 | Fitzgerald et al. | 2005/0187547 A1 | 8/2005 | Sugi |
| 7,344,268 B2 | 3/2008 | Jigamian | 2005/0197659 A1 | 9/2005 | Bahney |
| 7,367,976 B2 | 5/2008 | Lawes et al. | 2005/0203504 A1 | 9/2005 | Wham et al. |
| 2002/0013583 A1 | 1/2002 | Camran et al. | 2005/0240179 A1 | 10/2005 | Buysse et al. |
| 2002/0049442 A1 | 4/2002 | Roberts et al. | 2006/0052778 A1 | 3/2006 | Chapman et al. |
| 2002/0099372 A1 | 7/2002 | Schulze et al. | 2006/0064085 A1 | 3/2006 | Schechter et al. |
| 2002/0107517 A1 | 8/2002 | Witt et al. | 2006/0074417 A1 | 4/2006 | Cunningham et al. |
| 2002/0111624 A1 | 8/2002 | Witt et al. | 2006/0079888 A1 | 4/2006 | Mulier et al. |
| 2002/0188294 A1 | 12/2002 | Couture et al. | 2006/0079890 A1 | 4/2006 | Guerra |
| 2003/0014052 A1 | 1/2003 | Buysse et al. | 2006/0079891 A1 | 4/2006 | Arts et al. |
| 2003/0014053 A1 | 1/2003 | Nguyen et al. | 2006/0116675 A1 | 6/2006 | McClurken et al. |
| 2003/0018331 A1 | 1/2003 | Dycus et al. | 2006/0129146 A1 | 6/2006 | Dycus et al. |
| 2003/0018332 A1 | 1/2003 | Schmaltz et al. | 2006/0161150 A1 | 7/2006 | Keppel |
| 2003/0032956 A1 | 2/2003 | Lands et al. | 2006/0167450 A1 | 7/2006 | Johnson et al. |
| 2003/0069571 A1 | 4/2003 | Treat et al. | 2006/0167452 A1 | 7/2006 | Moses et al. |
| 2003/0078578 A1 | 4/2003 | Truckai et al. | 2006/0173452 A1 | 8/2006 | Buysse et al. |
| 2003/0109875 A1 | 6/2003 | Tetzlaff et al. | 2006/0189980 A1 | 8/2006 | Johnson et al. |
| 2003/0114851 A1 | 6/2003 | Truckai et al. | 2006/0189981 A1 | 8/2006 | Dycus et al. |
| 2003/0139741 A1 | 7/2003 | Goble et al. | 2006/0190035 A1 | 8/2006 | Hushka et al. |
| 2003/0139742 A1 | 7/2003 | Wampler et al. | 2006/0217709 A1 | 9/2006 | Couture et al. |
| 2003/0158549 A1 | 8/2003 | Swanson | 2006/0224158 A1 | 10/2006 | Odom et al. |
| 2003/0181910 A1 | 9/2003 | Dycus et al. | 2006/0259036 A1 | 11/2006 | Tetzlaf et al. |
| 2003/0199869 A1 | 10/2003 | Johnson et al. | 2006/0264922 A1 | 11/2006 | Sartor et al. |
| 2003/0216732 A1 | 11/2003 | Truckai et al. | 2006/0264931 A1 | 11/2006 | Chapman et al. |
| 2003/0220637 A1 | 11/2003 | Truckai et al. | 2006/0271038 A1 | 11/2006 | Johnson et al. |
| 2003/0229344 A1 | 12/2003 | Dycus et al. | 2006/0287641 A1 | 12/2006 | Perlin |
| 2003/0236325 A1 | 12/2003 | Bonora | 2007/0016182 A1 | 1/2007 | Lipson et al. |
| 2004/0030330 A1 | 2/2004 | Brassell et al. | 2007/0016187 A1 | 1/2007 | Weinberg et al. |
| 2004/0030332 A1 | 2/2004 | Knowlton et al. | 2007/0043352 A1 | 2/2007 | Garrison et al. |
| 2004/0049185 A1 | 3/2004 | Latterell et al. | 2007/0043353 A1 | 2/2007 | Dycus et al. |
| 2004/0064151 A1 | 4/2004 | Mollenauer | 2007/0055231 A1 | 3/2007 | Dycus et al. |
| 2004/0078035 A1 | 4/2004 | Kanehira et al. | 2007/0060919 A1 | 3/2007 | Isaacson et al. |
| 2004/0082952 A1* | 4/2004 | Dycus et al. ............. 606/51 | 2007/0062017 A1 | 3/2007 | Dycus et al. |
| 2004/0087943 A1 | 5/2004 | Dycus et al. | 2007/0074807 A1 | 4/2007 | Guerra |
| 2004/0115296 A1 | 6/2004 | Duffin | 2007/0078456 A1 | 4/2007 | Dumbauld et al. |
| 2004/0116924 A1 | 6/2004 | Dycus et al. | 2007/0078458 A1 | 4/2007 | Dumbauld et al. |
| 2004/0116979 A1 | 6/2004 | Truckai et al. | 2007/0078459 A1 | 4/2007 | Johnson et al. |
| 2004/0122423 A1 | 6/2004 | Dycus et al. | 2007/0088356 A1 | 4/2007 | Moses et al. |
| 2004/0143263 A1 | 7/2004 | Schechter et al. | 2007/0106295 A1 | 5/2007 | Garrison et al. |
| 2004/0147925 A1 | 7/2004 | Buysse et al. | 2007/0106297 A1 | 5/2007 | Dumbauld et al. |
| 2004/0162557 A1 | 8/2004 | Tetzlaff et al. | 2007/0118111 A1 | 5/2007 | Weinberg |
| 2004/0176762 A1 | 9/2004 | Lawes et al. | 2007/0118115 A1 | 5/2007 | Artale et al. |
| 2004/0193153 A1 | 9/2004 | Sarter et al. | 2007/0142833 A1 | 6/2007 | Dycus et al. |
| 2004/0225288 A1 | 11/2004 | Buysse et al. | 2007/0142834 A1 | 6/2007 | Dumbauld |
| 2004/0230189 A1 | 11/2004 | Keppel | 2007/0156139 A1 | 7/2007 | Schechter et al. |
| 2004/0236325 A1 | 11/2004 | Tetzlaff et al. | 2007/0156140 A1 | 7/2007 | Baily |
| 2004/0236326 A1 | 11/2004 | Schulze et al. | 2007/0173811 A1 | 7/2007 | Couture et al. |
| 2004/0243125 A1 | 12/2004 | Dycus et al. | 2007/0173814 A1 | 7/2007 | Hixson et al. |
| 2004/0249371 A1 | 12/2004 | Dycus et al. | 2007/0179499 A1 | 8/2007 | Garrison |
| 2004/0249374 A1 | 12/2004 | Tetzlaff et al. | 2007/0203485 A1 | 8/2007 | Keppel |
| 2004/0250419 A1 | 12/2004 | Sremcich et al. | 2007/0213706 A1 | 9/2007 | Dumbauld et al. |

| | | | | | | |
|---|---|---|---|---|---|---|
| 2007/0213707 A1 | 9/2007 | Dumbauld et al. | GB | 2213416 | 8/1989 | |
| 2007/0213708 A1 | 9/2007 | Dumbauld et al. | JP | 501068 | 9/1984 | |
| 2007/0213712 A1 | 9/2007 | Buysse et al. | JP | 502328 | 3/1992 | |
| 2007/0255279 A1 | 11/2007 | Buysse et al. | JP | 5-5106 | 1/1993 | |
| 2007/0260235 A1 | 11/2007 | Podhajsky | JP | 5-40112 | 2/1993 | |
| 2007/0260238 A1 | 11/2007 | Guerra | JP | 06343644 A2 | 12/1994 | |
| 2007/0260241 A1 | 11/2007 | Dalla Betta et al. | JP | 07265328 A2 | 10/1995 | |
| 2007/0260242 A1 | 11/2007 | Dycus et al. | JP | 08056955 A2 | 3/1996 | |
| 2007/0265616 A1 | 11/2007 | Couture et al. | JP | 08252263 A2 | 10/1996 | |
| 2008/0004616 A1 | 1/2008 | Patrick | JP | 09010223 A2 | 1/1997 | |
| 2008/0009860 A1 | 1/2008 | Odom | JP | 11244298 A2 | 9/1999 | |
| 2008/0015575 A1 | 1/2008 | Odom et al. | JP | 2000342599 A2 | 12/2000 | |
| 2008/0021450 A1 | 1/2008 | Couture | JP | 2000350732 A2 | 12/2000 | |
| 2008/0033428 A1 | 2/2008 | Artale et al. | JP | 2001008944 A2 | 1/2001 | |
| 2008/0039835 A1 | 2/2008 | Johnson et al. | JP | 2001029356 A2 | 2/2001 | |
| 2008/0045947 A1 | 2/2008 | Johnson et al. | JP | 2001128990 A2 | 5/2001 | |
| 2008/0058802 A1 | 3/2008 | Couture et al. | RU | 401367 | 11/1974 | |
| 2008/0082100 A1 | 4/2008 | Orton et al. | WO | WO89/00757 | 1/1989 | |

FOREIGN PATENT DOCUMENTS

| | | | | | |
|---|---|---|---|---|---|
| DE | 2415263 | 10/1975 | WO | WO 92/04873 | 4/1992 |
| DE | 2627679 | 1/1977 | WO | WO 92/06642 | 4/1992 |
| DE | 8712328 | 3/1988 | WO | WO 94/08524 A | 4/1994 |
| DE | 4303882 | 8/1994 | WO | WO94/20025 | 9/1994 |
| DE | 29616210 | 1/1997 | WO | WO 95/02369 | 1/1995 |
| DE | 19608716 | 4/1997 | WO | WO95/07662 | 3/1995 |
| DE | 19751106 | 5/1998 | WO | WO 95/07662 | 3/1995 |
| DE | 19751108 | 5/1999 | WO | WO95/15124 | 6/1995 |
| EP | 0364216 A1 | 4/1990 | WO | WO 96/22056 | 7/1995 |
| EP | 518230 A1 | 12/1992 | WO | WO96/05776 | 2/1996 |
| EP | 0 541 930 B1 | 5/1993 | WO | WO 96/13218 | 9/1996 |
| EP | 0572131 | 12/1993 | WO | WO 97/00646 | 1/1997 |
| EP | 584787 A1 | 3/1994 | WO | WO 97/00647 | 1/1997 |
| EP | 0589453 A2 | 3/1994 | WO | WO 97/10764 | 3/1997 |
| EP | 0623316 A1 | 11/1994 | WO | WO97/10764 | 3/1997 |
| EP | 0624348 A2 | 11/1994 | WO | WO 97/24073 | 7/1997 |
| EP | 0650701 A1 | 5/1995 | WO | WO 97/24993 | 7/1997 |
| EP | 0694290 A3 | 3/1996 | WO | WO 98/27880 | 7/1998 |
| EP | 0717966 A1 | 8/1996 | WO | WO 99/03407 | 1/1999 |
| EP | 0754437 A3 | 3/1997 | WO | WO 99/03408 | 1/1999 |
| EP | 853922 A1 | 7/1998 | WO | WO 99/03409 | 1/1999 |
| EP | 0875209 A1 | 11/1998 | WO | WO 99/12488 | 3/1999 |
| EP | 0878169 A1 | 11/1998 | WO | WO 99/40857 | 8/1999 |
| EP | 0887046 A3 | 1/1999 | WO | WO 99/40861 | 8/1999 |
| EP | 0923907 A1 | 6/1999 | WO | WO 99/51158 | 10/1999 |
| EP | 0986990 A1 | 3/2000 | WO | WO 99/66850 | 12/1999 |
| EP | 1034747 A1 | 9/2000 | WO | WO 99/66850 A | 12/1999 |
| EP | 1034748 A1 | 9/2000 | WO | WO 00/24330 | 5/2000 |
| EP | 1025807 A3 | 10/2000 | WO | WO 00/24331 | 5/2000 |
| EP | 1034746 A3 | 10/2000 | WO | WO 00/41638 | 7/2000 |
| EP | 1050278 A1 | 11/2000 | WO | WO00/47124 | 8/2000 |
| EP | 1053719 A1 | 11/2000 | WO | WO 00/53112 | 9/2000 |
| EP | 1053720 A1 | 11/2000 | WO | WO02/080783 | 10/2000 |
| EP | 1055399 A1 | 11/2000 | WO | WO 01/17448 A | 3/2001 |
| EP | 1055400 A1 | 11/2000 | WO | WO 01/54604 | 8/2001 |
| EP | 1080694 A1 | 3/2001 | WO | WO 02/07627 | 1/2002 |
| EP | 1082944 A1 | 3/2001 | WO | WO02/07627 | 1/2002 |
| EP | 1159926 A2 | 12/2001 | WO | WO 02/067798 A1 | 9/2002 |
| EP | 1301135 A | 4/2003 | WO | WO 02/080783 | 10/2002 |
| EP | 1330991 A1 | 7/2003 | WO | WO 02/080784 | 10/2002 |
| EP | EP1486177 A2 | 6/2004 | WO | WO02/080784 | 10/2002 |
| EP | 1472984 A1 | 11/2004 | WO | WO02/080785 | 10/2002 |
| EP | 1527747 A2 | 5/2005 | WO | WO 02/080785 | 10/2002 |
| EP | 1530952 A1 | 5/2005 | WO | WO02/080786 | 10/2002 |
| EP | 1532932 A1 | 5/2005 | WO | WO 02/080788 | 10/2002 |
| EP | 1535581 A2 | 6/2005 | WO | WO02/080793 | 10/2002 |
| EP | 1609430 A1 | 12/2005 | WO | WO 02/080794 | 10/2002 |
| EP | 1632192 A1 | 3/2006 | WO | WO02/080794 | 10/2002 |
| EP | 1645238 A1 | 4/2006 | WO | WO 02/080795 | 10/2002 |
| EP | 1645240 A2 | 4/2006 | WO | WO 02/080796 | 10/2002 |
| EP | 1707143 A1 | 10/2006 | WO | WO02/080797 | 10/2002 |
| GB | 2214430 A | 6/1989 | WO | WO 02/080797 | 10/2002 |
| | | | WO | WO 02/080798 | 10/2002 |
| | | | WO | WO 02/080799 | 10/2002 |

| | | |
|---|---|---|
| WO | WO02/081170 | 10/2002 |
| WO | WO 02/081170 | 10/2002 |
| WO | WO00/24331 | 5/2003 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO2004/082495 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |
| WO | WO 05/110264 | 11/2005 |

OTHER PUBLICATIONS

Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparispn of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Used of the LigaSure Vessel Sealing System in Urological Cancer Surger" Grand Rounds in Urology 1999 vol. 1 Issue 4 pp. 10-17.
Rothenberg et al. "Use of the LigaSure Vessel Sealing in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostatis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdonimal Surgery" Innovations That Work, Jun. 2002.
Levy et al. "Randomized Trial of Suture Versus Electrosurgical Bipolar Vessel Seating in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al, "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle et al., "Laparoscopic Palomo Varicocale Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.

Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Searcg Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 0506399 dated Jan. 5, 2006.
Int'l Search Report EP 1683496 dated Jun. 2006.
Int'l Search Report EP 04013772 dated Apr. 1, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.5 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.

* cited by examiner

ELECTROSURGICAL FORCEPS WITH ENERGY BASED TISSUE DIVISION

BACKGROUND

1. Technical Field

The present disclosure relates to an electrosurgical instrument and method for performing electrosurgical procedures. More particularly, the present disclosure relates to an open or endoscopic bipolar electrosurgical forceps including opposing jaw members which include an energy-based cutting element (e.g., cutting electrode) for energy based tissue division.

2. Background of Related Art

A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive plates which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Since tissue sealing procedures involve more than simply cauterizing tissue, to create an effective seal the procedures involve precise control of a variety of factors. In order to affect a proper seal in vessels or tissue, it has been determined that two predominant mechanical parameters must be accurately controlled: the pressure applied to the tissue; and the gap distance between the electrodes (i.e., distance between opposing jaw members when closed about tissue).

Many of the instruments of the past include blade members or shearing members which simply cut tissue in a mechanical and/or electromechanical manner. Other instruments generally rely on clamping pressure alone to procure proper sealing thickness and are often not designed to take into account gap tolerances and/or parallelism and flatness requirements which are parameters which, if properly controlled, can assure a consistent and effective tissue seal.

In addition, conventional or known tissue sealing reciprocating instruments have cutting mechanisms which are primarily designed to mechanically divide tissue (i.e., knife blade) and do not divide tissue in an electrosurgical fashion.

Thus, a need exists to develop an electrosurgical instrument which effectively and consistently seals, coagulates or cauterizes tissue and which is selectively configurable to cut tissue in an electrosurgical fashion.

SUMMARY

The present disclosure relates to a vessel or tissue sealing and dividing instrument which is designed to manipulate, grasp and seal tissue utilizing jaw members which are configured to close about tissue to produce a highly effective tissue seal. The instrument includes a pair of jaw members configured for sealing tissue and an energy-based cutting element attached at two or more pivot points to the jaw members. When the jaw members are open, the cutting element is deployed and the instrument can be used to divide tissue. When the jaw members are closed about tissue and the instrument can be used to seal tissue.

One embodiment according to the present disclosure relates to an electrosurgical bipolar forceps for sealing and dividing tissue. An electrosurgical bipolar forceps for sealing and dividing tissue is disclosed. The forceps includes one or more shaft members having an end effector assembly disposed at a distal end thereof. The end effector assembly includes two jaw members movable from a first position to a second position wherein the jaw members cooperate to grasp tissue therebetween. Each of the jaw members includes an electrically conductive surface adapted to connect to a first energy source which communicates electrosurgical energy through tissue held therebetween. The forceps also include an energy-based cutting element adapted to connect to a second energy source and disposed between the jaw members. The energy-based cutting element is moveable from a first configuration when said jaw members are in the first position to a second configuration wherein the energy-based cutting element is disposed at an angle between the jaw members.

Another embodiment according to the present disclosure relates to a method. The method includes the steps of providing an electrosurgical bipolar forceps. The forceps includes two jaw members movable from a first position to a second position wherein the jaw members cooperate to grasp tissue therebetween. Each of the jaw members includes an electrically conductive surface adapted to connect to a first energy source which communicates electrosurgical energy through tissue held therebetween. The forceps also include an energy-based cutting element adapted to connect to a second energy source and disposed between the jaw members. The energy-based cutting element is moveable from a first configuration when said jaw members are in the first position to a second configuration wherein the energy-based cutting element is disposed at an angle between the jaw members. The method also includes the steps of positioning the jaw members in the first position to deploy the energy-based cutting element, supplying electrosurgical energy to the energy-based cutting element, and moving electrosurgical bipolar forceps to position the energy-based cutting element in operative proximity to tissue thereby cutting tissue.

A further embodiment according to the present disclosure relates to another method. The method includes the steps of providing an electrosurgical bipolar forceps. The forceps includes two jaw members movable from a first position to a second position wherein the jaw members cooperate to grasp tissue therebetween. Each of the jaw members includes an electrically conductive surface adapted to connect to a first energy source which communicates electrosurgical energy through tissue held therebetween. The forceps also include an energy-based cutting element adapted to connect to a second energy source and disposed between the jaw members. The energy-based cutting element is moveable from a first configuration when said jaw members are in the first position to a second configuration wherein the energy-based cutting element is disposed at an angle between the jaw members. The method also includes the steps of positioning the jaw members into the subsequent position wherein the jaw members cooperate to grasp tissue therebetween and communicating electrosurgical energy through tissue held therebetween thereby sealing tissue.

BRIEF DESCRIPTION OF THE DRAWINGS

Various embodiments of the present disclosure are described herein with reference to the drawings wherein.

DETAILED DESCRIPTION

Particular embodiments of the present disclosure will be described hereinbelow with reference to the accompanying drawings. In the following description, well-known functions or constructions are not described in detail to avoid obscuring the present disclosure in unnecessary detail.

Figure 1:
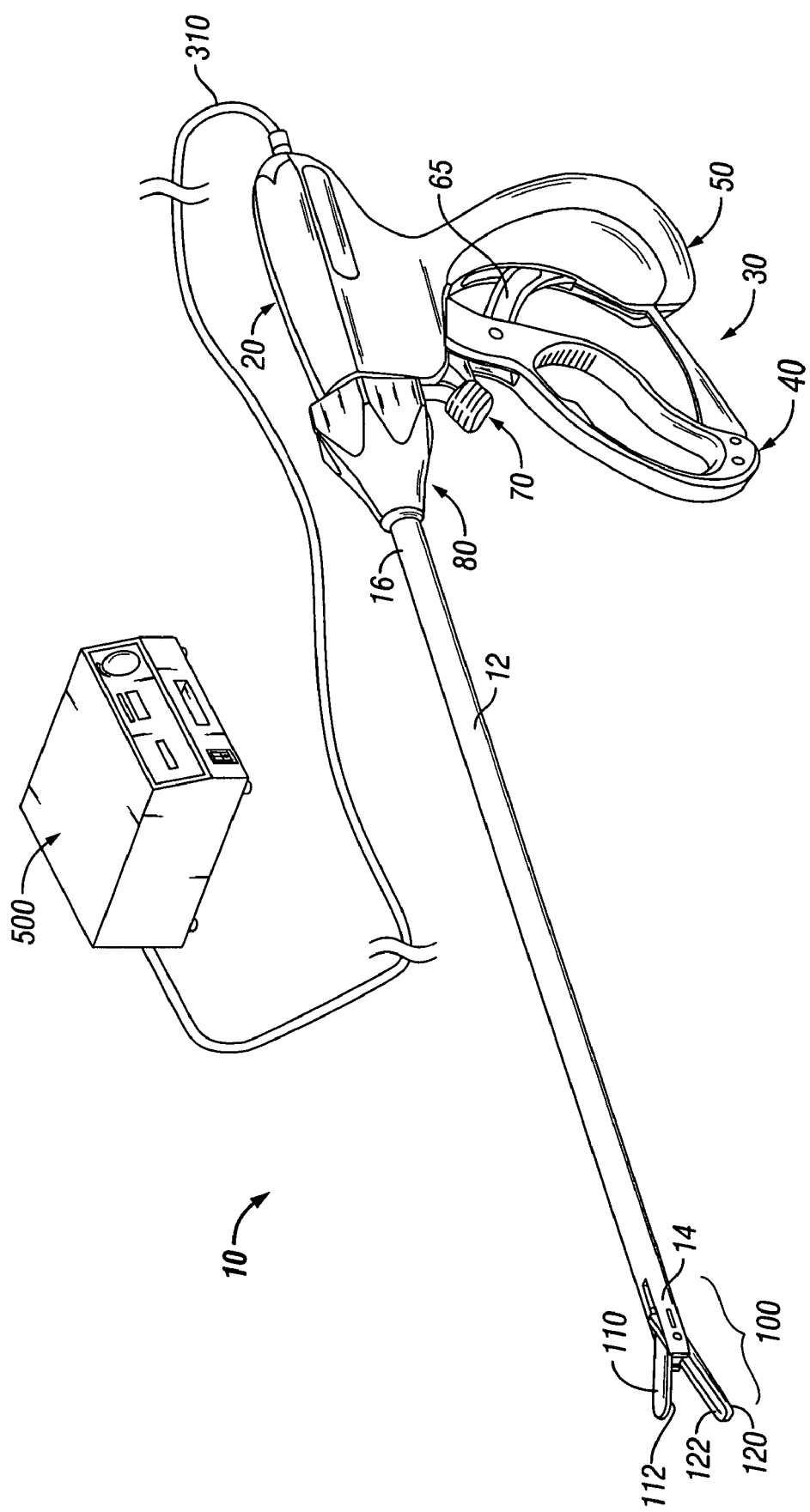
FIG. 1 is a perspective view of an endoscopic bipolar forceps having a cutting element according to the present disclosure.

FIG. 1 shows an endoscopic vessel sealing bipolar forceps 10. Those skilled in the art will understand that the invention according to the present disclosure may be adapted for use with either an endoscopic instrument or an open instrument. It should also be appreciated that different electrical and mechanical connections and other considerations apply to each particular type of instrument, however, the novel aspects with respect to the energy-based cutting element for energy based tissue division are generally consistent with respect to both the open or endoscopic designs. Moreover and as described herein, the various figures show vessel sealin instruments for use with energy-based cutting element, however other instruments may be configured to use the same or similar cutting element, e.g., cauterizing instruments, coagulators, etc.

In the drawings and in the description which follows, the term "proximal", refers to the end of the forceps 10 which is closer to the user, while the term "distal" refers to the end of the forceps which is further from the user.

FIGS. 1-4 show the forceps 10 which is configured to support an effector assembly 100. More particularly, forceps 10 generally includes a housing 20, a handle assembly 30, a rotating assembly 80, and a trigger assembly 70 which mutually cooperate with the end effector assembly 100 to grasp, seal and, if required, divide tissue. The forceps 10 also includes a shaft 12 which has a distal end 14 which mechanically engages the end effector assembly 100 and a proximal end 16 which mechanically engages the housing 20 proximate the rotating assembly 80.

Figure 2:
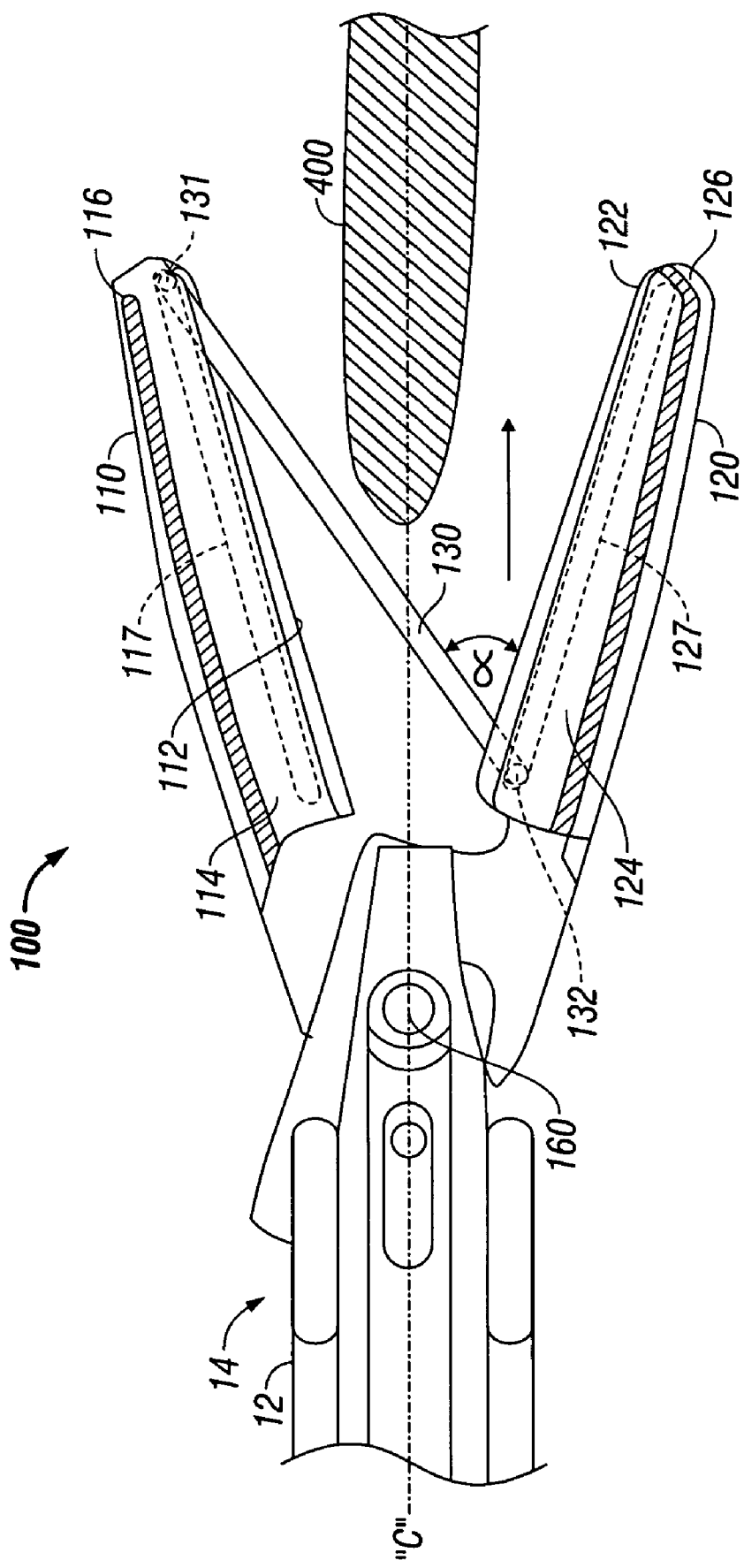
FIG. 2 is a side, partial internal view of an endoscopic forceps showing a cutting electrode in a deployed configuration according to the present disclosure.

The forceps 10 also includes a plug (not shown) which connects the forceps 10 to a source of electrosurgical energy, e.g., an electrosurgical generator 500, via an electrical cable 310. Handle assembly 30 includes a fixed handle 50 and a movable handle 40. Handle 40 moves relative to the fixed handle 50 to actuate the end effector assembly 100 and enable a user to grasp and manipulate tissue 400 as shown in FIG. 2.

The end effector assembly 100 includes a pair of opposing jaw members 110 and 120 each having an electrically conductive sealing plate 112 and 122, respectively, attached thereto for conducting electrosurgical energy through tissue 400 held therebetween. More particularly, the jaw members 110 and 120 move in response to movement of the handle 40 from an open position to a closed position. In open position the sealing plates 112 and 122 are disposed in spaced relation relative to one another. In a clamping or closed position the sealing plates 112 and 122 cooperate to grasp tissue and apply electrosurgical energy thereto.

The jaw members 110 and 120 are activated using a drive assembly (not shown) enclosed within the housing 20. The drive assembly cooperates with the movable handle 40 to impart movement of the jaw members 110 and 120 from the open position to the clamping or closed position. Examples of a handle assemblies are shown and described in commonly-owned U.S. application Ser. No. 10/389,894 entitled "VESSEL SEALER AND DIVIDER AND METHOD MANUFACTURING SAME" and commonly owned U.S. application Ser. No. 10/460,926 entitled "VESSEL SEALER AND DIVIDER FOR USE WITH SMALL TROCARS AND CANNULAS" which are both hereby incorporated by reference herein in their entirety.

In addition, the handle assembly 30 of this particular disclosure includes a four-bar mechanical linkage which provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing plates 112 and 122 in a closed position against the tissue. The details relating to the inter-cooperative relationships of the inner-working components of forceps 10 are disclosed in the above-cited commonly-owned U.S. patent application Ser. No. 10/369,894. Another example of an endoscopic handle assembly which discloses an off-axis, lever-like handle assembly, is disclosed in the above-cited U.S. patent application Ser. No. 10/460,926.

The forceps 10 also includes a rotating assembly 80 mechanically associated with the shaft 12 and the drive assembly (not shown). Movement of the rotating assembly 80 imparts similar rotational movement to the shaft 12 which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. Nos. 10/369,894 and 10/460,926.

As best seen with respect to FIGS. 1-2, the end effector assembly 100 attaches to the distal end 14 of shaft 12. The jaw members 110 and 120 are preferably pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 20 and handle assembly 30. In either of these two instances, the forceps 10 may be either partially disposable or reposable, such as where a new or different end effector assembly 100 or end effector assembly 100 and shaft 12 are used to selectively replace the old end effector assembly 100 as needed.

Figure 4:
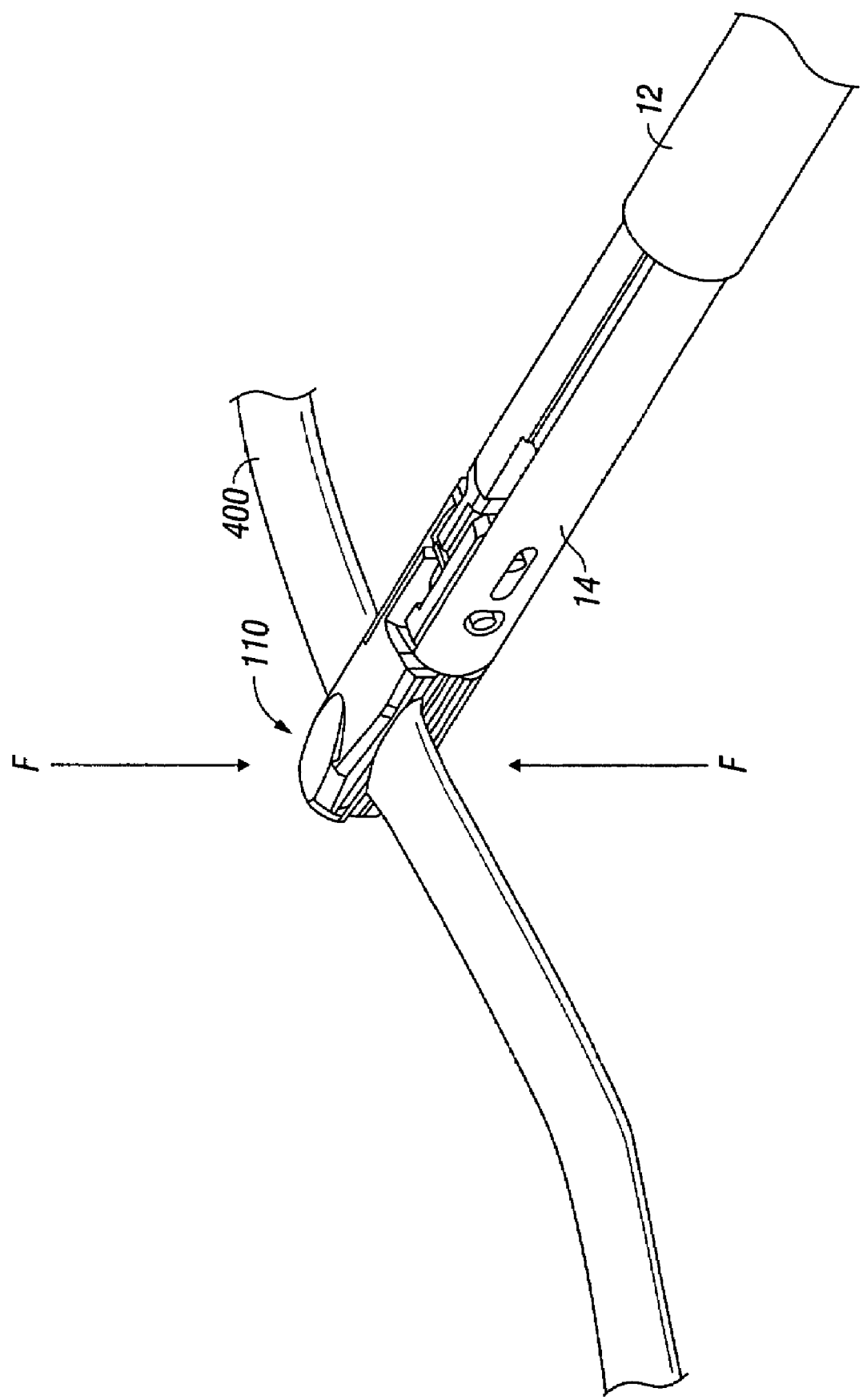
FIG. 4 is a rear, perspective view of the end effector of FIG. 3A shown with tissue grasped therein.

Since the forceps 10 applies energy through electrodes, each of the jaw members 110 and 120 includes a pair of electrically conductive surfaces 112, 122 respectively, disposed on an inner-facing surface thereof. Thus, once the jaw members 110 and 120 are fully compressed about the tissue 400, the forceps 10 is now ready for selective application of electrosurgical energy as shown in FIG. 4. In order to seal tissue, the tissue grasped by the jaw members 110, 120 under a specified closure pressure from about 3 kg/cm$^2$ to about 16 kg/cm$^2$ and the jaw members 110, 120 are designed to maintain a gap from about 0.001 inches to about 0.006 inches. At that point, the electrically conductive surfaces 112 and 122 cooperate to seal tissue 400 held therebetween upon the application of electrosurgical energy. Jaw members 110 and 120 also include insulators 116 and 126 which together with the outer, non-conductive plates of the jaw members 110 and 120 are configured to limit and/or reduce many of the known undesirable effects related to tissue sealing, e.g., flashover, thermal spread and stray current dissipation.

With reference to FIGS. 2-3, an energy-based cutting element or center electrode 130 is deployable between electrically conductive surfaces 112, 122, respectively. The cutting element 130 may be an electrode configured to transmit electrosurgical energy, an ultrasonic probe configured to transmit ultrasonic energy or a thermal blade capable of transmitting heat to the tissue.

The cutting element 130 is attached to the jaw members 110 and 120 at two pivot points 131 and 132 respectively. The pivot points 131, 132 may include attachment mechanisms or mechanical interfaces 137, 139 (e.g., pins, shafts, etc.) which attach the cutting element 130 to the jaw members 110, 120 allowing the cutting element 130 to rotate freely therebetween (e.g., pass through holes). The pivot points 131, 132 may also include grooves or guides 117, 127 within the jaw members 110, 120 which allow the ends of the cutting element 130 to move freely during transitioning between open and close positions of the jaw members 110, 120.

It is envisioned that the cutting element 130 can be shaped in a variety of geometrical configurations to provide an optimal cutting surface. For instance, the cutting element 130 may have a circular, rectangular, triangular horizontal cross section.

The pivot points 131, 132 are positioned at opposite ends of jaw members 110 and 120, respectively. More specifically, pivot point 131 is positioned at a distal end 116 of the jaw member 110 and pivot point 132 is positioned at a proximal end of the jaw member 120. The pivots 131, 132 move within groves on guides 117, 127 in jaw members 110, 120 respectively. This configuration allows the cutting element 130 to be automatically deployed when the jaw members 110, 120 are in open position so that the cutting element 130 intersects the center plane "C." It is envisioned that the pivot points 131, 132 may be oriented in a plurality of ways which permit the cutting element 130 to be deployed at various angles "α" when the jaw members 110, 120 are open. For instance, the pivot point 131 may be disposed more towards the proximal end of jaw member 110 to increase the cutting angle the pivot point 132 may be disposed more towards the distal end of jaw member 120 depending upon a particular purpose. The cutting angle may also be dependent in the relative opening of the jaw members 110, 120, i.e., the relative distance between the jaw members 110, 120 when opened.

Figure 3A:
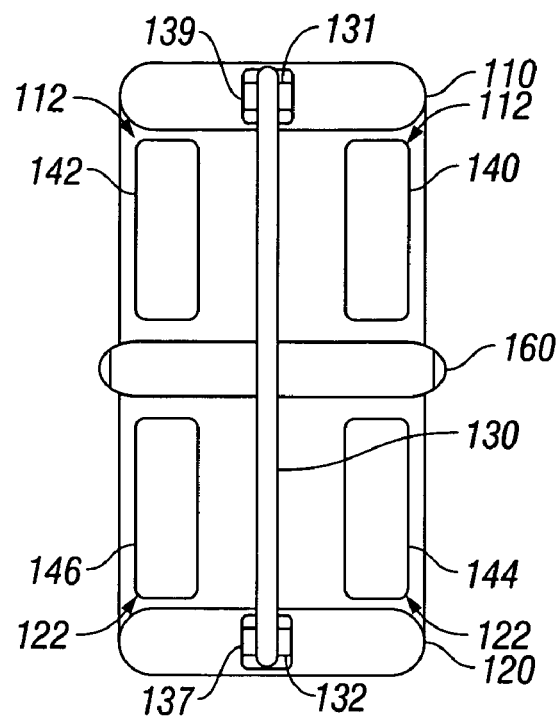
FIG. 3A is a front view of another end effector assembly according to the present disclosure.
Figure 3B:
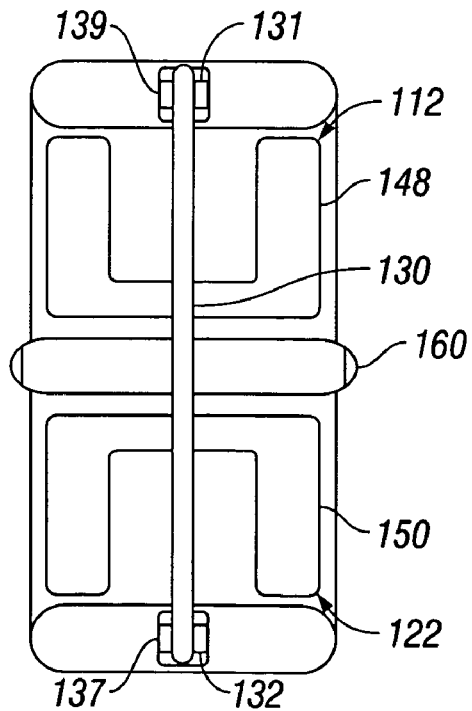
FIG. 3B is a front view of another end effector assembly according to the present disclosure.

As shown in FIG. 3A, the electrically conductive surfaces 112, 122 may include electrically conductive plates 140, 142, 144, 146. This permits the cutting element 130 to be attached to the jaw members 110, 120 in an unimpeded fashion, i.e., without contacting the conductive surfaces 112, 122. It is envisioned that the electrically conductive surfaces 112, 122 may include any number of electrically conductive plates, such as for instance, a single electrically conductive plate 148, 150 disposed on each jaw member 110, 120, as shown in FIG. 3B, or eight plates (not shown), etc. The single electrically conductive plate 148 may be shaped in a number of forms, such as a "U" shape, a "H" shape. It is also envisioned that the electrically conductive plate 148 may be oriented in a plurality of ways. In addition, the single conductive plate 148 may be shaped to substantially match the surface of the jaw members 110, 120 with an opening for the pivot points 131, 132.

The ability of the cutting element 130 to automatically fold and raise as the jaw members 110, 120 are opened and closed respectively, allows the forceps 10 to have two modes of operation: a sealing mode and a cutting mode. During sealing mode, the jaw members 110 and 120 are clamped down in direction F as shown in FIG. 4 around tissue. The cutting element 130 folds down and the electrically conductive plates 140, 142, 144, 146 are energized thereby sealing tissue. Clamping of the jaw members 110, 120 is accomplished by moving the handle 40 relative to the fixed handle 50 to actuate the end effector assembly 100. The electrically conductive plates 140, 142, 144, 146 may be selectively energized once the jaw members 110, 120 are closed about tissue. The center electrode 130 in its folding orientation may be energized when the jaw members are closed to allow the user to selectively ct tissue after the seal has been formed. Alternatively, the center electrode or cutting element 130 may be energized when the jaw members are closed about tissue without prior sealing. It is envisioned that an alarm (not shown) may be included in this instance to warn the user that the tissue has not been treated prior to separation.

During an open cutting mode the jaw members 110 and 120 are open such that the cutting element 130 automatically deploys therebetween. As shown in FIGS. 1-4, forceps 10 also includes a trigger 70 which activates the generator 500 to supply electrosurgical energy or other types of energy depending on the type of the cutting element 130 used (e.g., ultrasonic, heat, etc.). The forceps 10 may be manually pushed toward and into tissue 400 as shown in FIG. 2 while the cutting element 130 is energized, thereby dividing the tissue along the longitudinal axis of the forceps 10.

Figure 5:
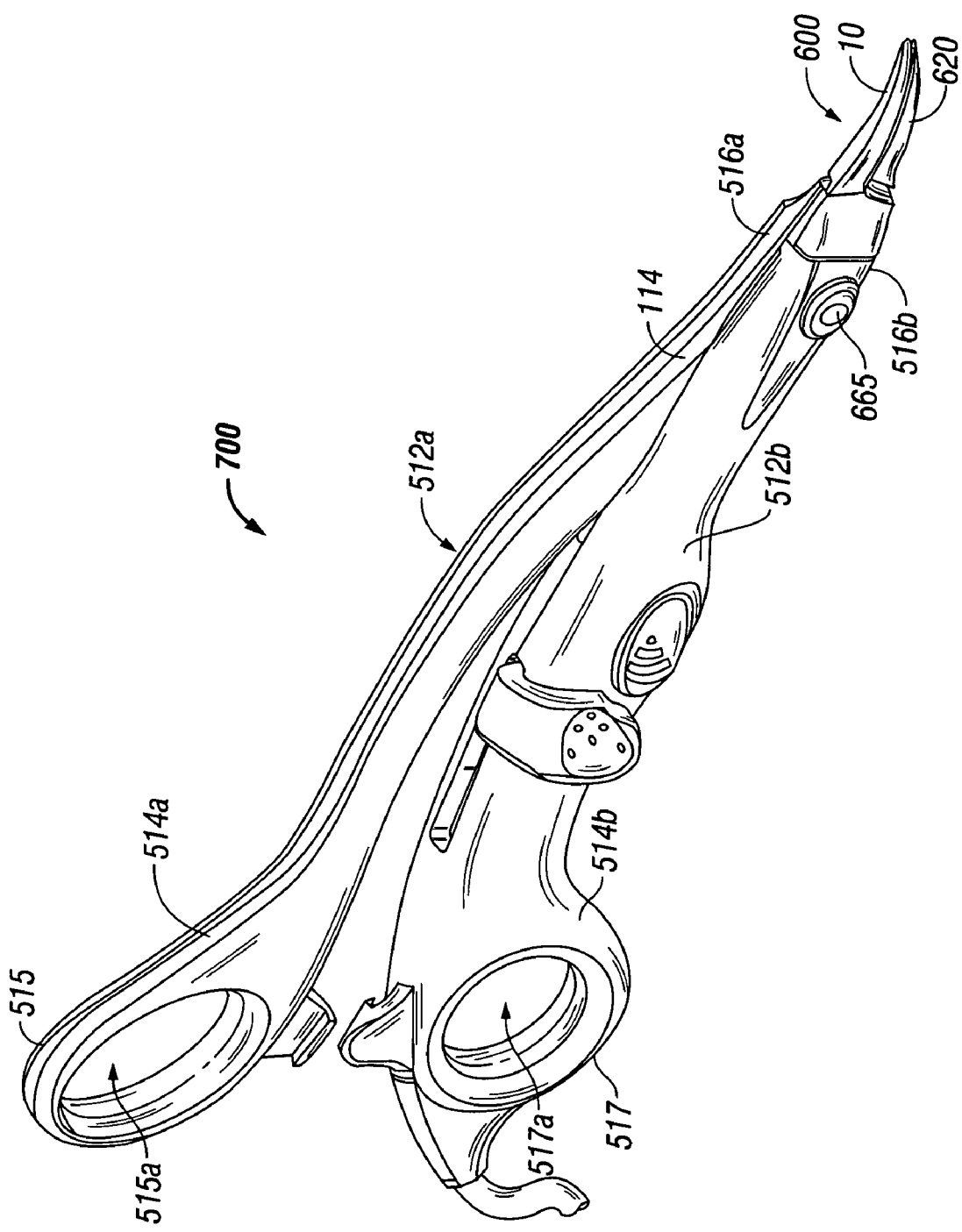
FIG. 5 is a perspective view of an open bipolar forceps having a cutting element according to the present disclosure.

From the foregoing and with reference to the various figure drawings, those skilled in the art will appreciate that certain modifications can also be made to the present disclosure without departing from the scope of the same. For example and as mentioned above, it is contemplated that any of the various jaw arrangements and cutting elements disclosed herein may be employed on an open forceps such as the open forceps 700 shown in FIG. 5. The forceps 700 includes an end effector assembly 600 which is attached to the distal ends 516a and 516b of shafts 512a and 512b, respectively. The end effector assembly 600 includes pair of opposing jaw members 610 and 620 which are pivotally connected about a pivot pin 665 and which are movable relative to one another to grasp vessels and/or tissue. Each of the opposing jaw members 610, 620 include electrically conductive surfaces 112, 122 and cutting element 130 disposed therebetween. When in an open configuration, the cutting element 130 deployed and the open forceps 700 may be used for dividing tissue when the cutting element 130 is selectively energized similar to the endoscopic forceps 10 described above. The open forceps 700 may also be used for clamping tissue for sealing, coagulation or cauterization without energizing the cutting element 130.

Each shaft 512a and 512b includes a handle 515 and 517, respectively, disposed at the proximal end 514a and 514b thereof which each define a finger hole 515a and 517a, respectively, therethrough for receiving a finger of the user. Finger holes 515a and 517a facilitate movement of the shafts 512a and 512b relative to one another which, in turn, pivot the jaw members 610 and 620 from an open position wherein the jaw members 610 and 620 are disposed in spaced relation relative to one another to a clamping or closed position wherein the jaw members 610 and 620 cooperate to grasp tissue or vessels therebetween. Further details relating to one particular open forceps are disclosed in commonly-owned U.S. application Ser. No. 10/962,116 filed Oct. 8, 2004 entitled "OPEN VESSEL SEALING INSTRUMENT WITH CUTTING MECHANISM AND DISTAL LOCKOUT", the entire contents of which being incorporated by reference herein.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical bipolar forceps for treating tissue, comprising:
   at least one shaft member having an end effector assembly disposed at a distal end thereof, the end effector assembly including two jaw members movable from a first position in spaced relation relative to one another to at least one subsequent position wherein the jaw members cooperate to grasp tissue therebetween;
   each of the jaw members including an electrically conductive surface adapted to connect to a first energy source which communicates electrosurgical energy through tissue held therebetween; and
   an energy-based cutting element adapted to connect to a second energy source and disposed between the jaw members, the jaw members being configured to deploy the energy-based cutting element, said energy-based cutting element being moveable by the jaw members from a first configuration longitudinally disposed within said jaw members when said jaw members are disposed in said first position to a second configuration wherein said energy-based cutting element is disposed at an angle between said jaw members when said jaw members are in at least one subsequent position; said energy-based cutting element being pivotably engaged to said jaw members at two pivot points, a first pivot point located on one of said jaw members and a second pivot point located on the other of said jaw members.

2. An electrosurgical bipolar forceps for sealing and dividing tissue as in claim 1, wherein each of the electrically conductive surfaces comprises at least one electrically conductive sealing plate.

3. An electrosurgical bipolar forceps for sealing and dividing tissue as in claim 1, wherein the energy-based cutting element when disposed at an angle is configured for dividing tissue upon selective activation of the second energy source.

4. An electrosurgical bipolar forceps for sealing and dividing tissue as in claim 1, wherein the energy-based cutting element is an electrode configured to transmit electrosurgical energy.

5. An electrosurgical bipolar forceps for sealing and dividing tissue as in claim 1, wherein the energy-based cutting element is an ultrasonic probe configured to transmit ultrasonic energy.

6. An electrosurgical bipolar forceps for sealing and dividing tissue as in claim 1, wherein the energy-based cutting element is a thermal blade configured to transmit heat.

7. An electrosurgical bipolar forceps for sealing and dividing tissue as in claim 1, wherein each of the pivot points include mechanical interfaces which attach the energy-based cutting element to the respective jaw members allowing the energy-based cutting element to rotate freely thereabout.

8. An electrosurgical bipolar forceps for sealing and dividing tissue as in claim 1, wherein at least one of the pivot points is disposed at a proximal end of one of said jaw members and at least another of the pivot points is disposed at a distal end of the other of said jaw members.

9. An electrosurgical bipolar forceps for sealing and dividing tissue as in claim 1, further comprising:
   a rotating assembly mechanically associated with the shaft member, wherein rotation of the rotating assembly imparts similar rotational movement to the shaft member and the end effector assembly.

10. A method for electrically cutting tissue comprising the steps of: providing an electrosurgical bipolar forceps including:
    two jaw members movable from a first position in spaced relation relative to one another to at least one subsequent position wherein the jaw members cooperate to grasp tissue therebetween,
    each of the jaw members including an electrically conductive surface adapted to connect to a first energy source which communicates electrosurgical energy through tissue held therebetween, and
    an energy-based cutting element adapted to connect to a second energy source and disposed between the jaw members, the jaw members being configured to deploy the energy-based cutting element, said energy-based cutting element being moveable by the jaw members from a first configuration longitudinally disposed within said jaw members when said jaw members are disposed in said first position to a second configuration wherein said energy-based cutting element is disposed at an angle between said jaw members when said jaw members are in at least one subsequent position;
    said energy-based cutting element being pivotably engaged to said jaw members at two pivot points, a first pivot point located on one of said jaw members and a second pivot point located on the other of said jaw members;
    positioning the jaw members in the first position to deploy the energy-based cutting element;
    supplying electrosurgical energy to the energy-based cutting element; and
    moving electrosurgical bipolar forceps to position the energy-based cutting element in operative proximity to tissue thereby culling tissue.

11. A method for electrically cutting tissue according to claim 10, wherein each of the electrically conductive surfaces includes at least one electrically conductive sealing plate.

12. A method for electrically cutting tissue according to claim 10, wherein the energy-based cutting element when disposed at an angle is configured for dividing tissue upon selective activation of the second energy source.

13. A method for electrically cutting tissue according to claim 10, wherein each of the pivot points include mechanical interfaces which attach the energy-based cutting element to the respective jaw members allowing the energy-based cutting element to rotate freely thereabout.

14. A method for electrically cutting tissue according to claim 10, wherein at least one of the pivot points is disposed at a proximal end of one of said jaw members and at least another of the pivot points is disposed at a distal end of the other of said jaw members.

15. An electrosurgical bipolar forceps for treating tissue, comprising:

at least one shaft member having an end effector assembly disposed at a distal end thereof the end effector assembly including two jaw members movable from a first position in spaced relation relative to one another to at least one subsequent position wherein the jaw members cooperate to grasp tissue therebetween;

each of the jaw members including an electrically conductive surface adapted to connect to a first energy source which communicates electrosurgical energy through tissue held therebetween; and a cutting element disposed between the jaw members, the jaw members being configured to deploy the energy-based cutting element, the cutting element being pivotably movable at two pivot points, a first pivot point located at a proximal end of one of the jaw members and a second pivot point located at a distal end of the other of the jaw members, wherein the cutting element is movable from a first configuration longitudinally disposed within the jaw members when the jaw members are disposed in the first position to a second configuration wherein the cutting element is disposed at an angle between the jaw members when the jaw members are disposed in at least one subsequent position.

* * * * *